United States Patent [19]

Ebnöther et al.

[11] 4,072,756

[45] Feb. 7, 1978

[54] TRICYCLO PIPERIDINO KETONES AND SOPORIFIC COMPOSITIONS THEREOF

[75] Inventors: Anton Ebnöther, Arlesheim; Jean-Michel Bastian, Therwil; Fulvio Gadient; André Stoll, both of Birsfelden, all of Switzerland

[73] Assignee: Sandoz Ltd., Basel, Switzerland

[21] Appl. No.: 686,132

[22] Filed: May 13, 1976

Related U.S. Application Data

[63] Continuation-in-part of Ser. No. 468,374, May 9, 1974, abandoned.

[30] Foreign Application Priority Data

| May 17, 1973 | Switzerland | 7048/73 |
| May 17, 1973 | Switzerland | 7051/73 |
| May 17, 1973 | Switzerland | 7053/73 |
| May 17, 1973 | Switzerland | 7054/73 |
| May 17, 1973 | Switzerland | 7055/73 |
| May 17, 1973 | Switzerland | 7056/73 |
| May 17, 1973 | Switzerland | 7057/73 |

[51] Int. Cl.² ............... C07D 495/04; C07D 493/00; C07D 495/00

[52] U.S. Cl. .................. 424/267; 260/293.57; 260/293.58; 260/293.62

[58] Field of Search ............. 260/293.57, 293.58, 260/293.62; 424/267

[56] References Cited

U.S. PATENT DOCUMENTS

| 3,014,911 | 12/1961 | Engelhardt | 260/293 |
| 3,306,897 | 2/1967 | Renz et al. | 260/240 |
| 3,458,522 | 7/1969 | Galantay | 260/293.57 X |
| 3,470,188 | 9/1969 | Kaiser et al. | 260/293.4 |
| 3,491,103 | 1/1970 | Jucker et al. | 260/293.4 |
| 3,624,078 | 11/1971 | Jucker et al. | 260/240 TC |
| 3,682,930 | 8/1972 | Bourquin et al. | 260/293.57 |

FOREIGN PATENT DOCUMENTS

| 1,470,263 | 5/1969 | Germany | 260/293.57 |

OTHER PUBLICATIONS

Chemical Abstracts, vol. 83, p. 552 (1975), abstract No. 164155μ, Ebnoether et al., (German Offenlegungsschrift No. 2423721, 12/1974).

*Primary Examiner*—Henry R. Jiles
*Assistant Examiner*—Richard A. Schwartz
*Attorney, Agent, or Firm*—Gerald D. Sharkin; Robert S. Honor; Thomas O. McGovern

[57] ABSTRACT

The invention concerns novel compounds of the formula:

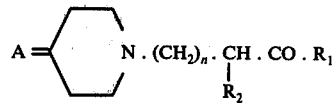

wherein $n$ is 1, 2 or 3
$R_1$ is lower alkyl
$R_2$ is hydrogen or lower alkyl and
A is a tricyclic moiety;

useful as sedative-neuroleptic, muscle-relaxant and sleep-promoting agents.

29 Claims, No Drawings

TRICYCLO PIPERIDINO KETONES AND SOPORIFIC COMPOSITIONS THEREOF

This is a continuation in part of our copending application Ser. No. 468,374 filed May 9th, 1974, now abandoned.

The present invention relates to new heterocyclic compounds.

In accordance with the invention there are provided new compounds of formula I,

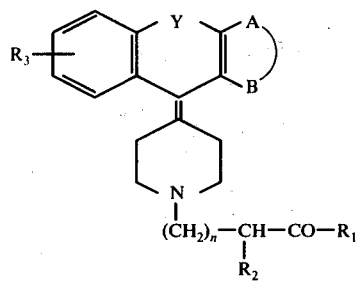

I wherein
$n$ is 1, 2 or 3,
$R_1$ is lower alkyl,
$R_2$ is hydrogen or lower alkyl,
$R_3$ is hydrogen, chlorine, bromine, fluorine, trifluoromethyl, lower alkyl, lower alkoxy or lower alkylthio,
A and B together with the double bond form a benzene ring, or a benzene ring substituted by chlorine, bromine, fluorine, trifluoromethyl, lower alkyl, lower alkoxy or lower alkylthio, or
A is sulphur and
A and B together with the double bond form a thiophene ring, or a thiophene ring substituted in the α position to the sulphur by chlorine, bromine or lower alkyl, and
Y is ethylene or vinylene, when A and B together with the double bond form a benzene ring, or a benzene ring substituted by chlorine, bromine, fluorine, trifluoromethyl, lower alkyl, lower alkoxy or lower alkylthio, or when A is sulphur and A and B together with the double bond form a thiophene ring, or a thiophene ring substituted in the α position to the sulphur by chlorine, bromine or lower alkyl, or
Y is oxygen, methyleneoxy, methylenethio or a group

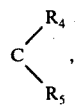

wherein $R_4$ and $R_5$ are independently lower alkyl, when A and B together with the double bond form a benzene ring, or a benzene ring substituted by chlorine, bromine, fluorine, trifluoromethyl, lower alkyl, lower alkoxy or lower alkylthio, or
Y is sulphur, when A is sulphur and A and B together with the double bond form a thiophene ring.

Further, in accordance with the invention a compound of formula I may be obtained by a process comprising alkylating a compound of formula II,

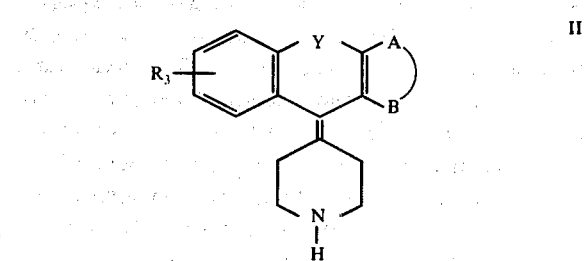

II wherein A, B, Y and $R_3$ are as defined above, with a compound of formula III, $$Z-CO-R_1 \quad \text{III}$$

wherein
$R_1$ is as defined above, and
Z is (a) X-$(CH_2)_n$—$CHR_2$— wherein $R_2$ and $n$ are as defined above, and X is the acid radical of a reactive ester, to produce a compound of formula I or
(b) $CH_2$=$CR_2$— wherein $R_2$ is as defined above, to produce a compound of formula I wherein $n$ is 1.

The substituent $R_2$ in the compounds of formula I preferably signifies hydrogen. When $R_2$ is lower alkyl, this alkyl group preferably contains 1 to 4 carbon atoms and especially signifies methyl. The radical $R_1$ preferably contains 1 to 4, especially 1 or 2 carbon atoms. The substituent $R_3$ preferably signifies hydrogen or chlorine. When $R_3$ is lower alkyl, this preferably contains 1 to 4 carbon atoms, when $R_3$ is lower alkoxy or alkylthio, these groups preferably contain 1 to 3 carbon atoms and especially signify methoxy or methylthio. When A and B together with the double bond form a benzene ring, this is preferably unsubstituted. When the benzene ring has a substituent, this preferably is chlorine. When the substituent of the benzene ring is lower alkyl, this preferably contains 1 to 4 carbon atoms and especially signifies methyl; when the substituent of the benzene ring is lower alkoxy or alkylthio, these groups preferably contain 1 to 3 carbon atoms and especially signify methoxy or methylthio.

When A is sulphur and A and B together with the double bond form a thiophene ring, this preferably is unsubstituted. When the thiophene ring has a substituent, this preferably is chlorine. When the substituent of the thiophene ring is lower alkyl, this preferably contains 1 to 4 carbon atoms and especially signifies methyl; when the substituent of the thiophene ring is lower alkoxy, this preferably contains 1 to 3 carbon atoms and especially signifies methoxy. Y preferably signifies oxygen or sulphur. When Y is a $$C \begin{matrix} R_4 \\ \\ R_5 \end{matrix}$$

group, the alkyl groups $R_4$ and $R_5$ preferably contain 1 to 3 carbon atoms and especially signify methyl groups. The number $n$ preferably is 1 or 2.

The preferred compounds are those wherein $R_1$ is methyl and $R_2$ is hydrogen. Especially suitable compounds are those wherein $R_1$ is methyl and $R_2$ is hydrogen, and A is sulphur and together with B and the double bond forms an unsubstituted thiophene ring, and either $R_3$ is hydrogen or chlorine and Y is sulphur, or $R_3$ is hydrogen and Y is a vinylene group. Compounds which are also especially suitable are those wherein $R_1$ is methyl, $R_2$ and $R_3$ are hydrogen and Y is oxygen, and A and B together with the double bond form an unsubstituted benzene ring.

The reaction of the invention of a compound of formula II with a compound of formula III may, for example, be effected in an inert organic solvent. The addition of a vinyl compound of formula IIIa,

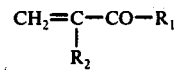
$$\text{IIIa}$$

wherein $R_1$ and $R_2$ are as defined above, to a compound of formula II is effected using as solvent, for example, a lower alkanol such as ethanol, or an ether, e.g. dioxane, and the reaction temperature preferably is between about 20° and 100° C. The reaction may conveniently be catalyzed by the addition of a strong base, e.g. benzyltrimethyl ammonium hydroxide. The reaction of a compound of formula II with a compound of formula IIIb,

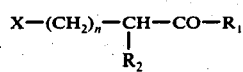
$$\text{IIIb}$$

wherein $R_1$, $R_2$, $n$ and X are as defined above, is preferably effected in the presence of an acid-binding agent. Suitable inert solvents are, for example, lower alkanols such as ethanol, chlorinated aliphatic hydrocarbons such as chloroform, or aromatic hydrocarbons such as toluene, or dimethyl formamide. Acid-binding agents which may be used are, for example, alkali metal carbonates such as sodium or potassium carbonate, or a tertiary nitrogen base such as triethylamine. The reaction is preferably effected at a temperature between about 50° and about 150° C, especially at the boiling temperature of the reaction mixture. X in the compounds of formula IIIb preferably signifies chlorine, bromine, iodine, or the acid radical of an organic sulphonic acid, e.g. the methylsulphonyloxy or the p-toluenesulphonyloxy radical.

The compounds of formula I may be isolated from the reaction mixture and purified in known manner, the free bases may be converted into acid addition salt forms thereof in the usual manner, and vice versa.

The starting materials of formula II may, for example, be obtained by reacting a ketone of formula IV,

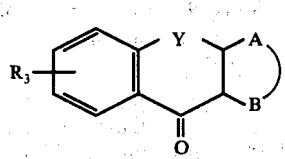
$$\text{IV}$$

wherein A, B, Y and $R_3$ are as defined above, with the Grignard compound of formula V,

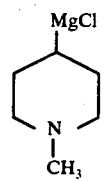
$$\text{V}$$

hydrolyzing the resulting complex, subsequently removing water and splitting off the methyl group in known manner from the resulting compound of formula VI,

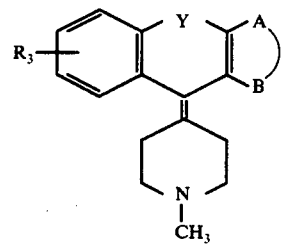
$$\text{VI}$$

wherein A, B, Y and $R_3$ are as defined above, e.g. by acylation with a compound of formula VII,

$$\text{VII}$$

and hydrolysis of the resulting urethane in known manner.

Compounds of formula VIa,

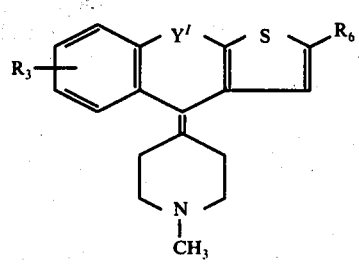
$$\text{VIa}$$

wherein $R_3$ is as defined above,
$Y^I$ is ethylene or vinylene, and
$R_6$ is lower alkyl,
may, for example, alternatively be obtained by acylating a compound of formula VIb,

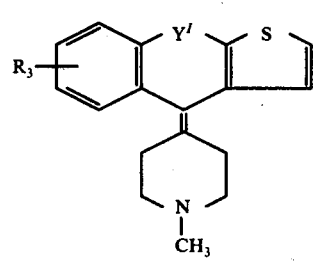
$$\text{VIb}$$

wherein $Y^I$ and $R_3$ are as defined above, and subsequently reducing the resulting acylation product.

The acylation of the compounds of formula VIb may be effected in known manner, e.g. by reacting the compound with suitable acid halides or acid anhydrides in the presence of an acid condensation agent, e.g. a strong acid such as phosphoric acid, at an elevated temperature, optionally with the addition of an inert organic solvent, or by acylating the compounds of formula VIb in a Friedel-Crafts reaction in the presence of a Friedel-Crafts catalyst. A formylation may be carried out in known manner with a mixture of hydrogen chloride and carbon monoxide in accordance with the method of Gattermann/Koch. The compounds of formula VIb may alternatively be formylated in accordance with the method of Vilsmeier and Haack with a substituted formamide and phosphorus oxychloride. The reduction of the acylation products may be effected in accordance with the usual methods for the reduction of the carbonyl group to the $CH_2$ group. Suitable reducing processes are, for example, the reduction in accordance with Clemmensen, e.g. with zinc/hydrochloric acid, or the method in accordance with Wolff-Kishner and modifications thereof, e.g. conversion of the acyl compounds into their hydrazones and subsequent treatment with a strong base.

Insofar as the production of the starting materials is not described, these are known or may be produced in accordance with known processes, or in a manner analogous to the processes described herein or to known processes.

Free base forms of compounds of formula I may be converted into acid addition salt forms in conventional manner and vice versa. Suitable inorganic acids include hydrochloric acid and hydrobromic acid. Suitable organic acids include fumaric acid.

In the following non-limitative Examples all temperatures are indicated in degrees Centigrade.

EXAMPLE 1

5-[4-(9-xanthenylidene)piperidino]-2-pentanone 7.2 g of 5-bromo-2-pentanone in 50 cc of chloroform are added dropwise to a suspension of 10.0 g of 4-(9-xanthenylidene)piperidine [M.P. 147°–149°, produced from N-methyl-4-(9-xanthenylidene)piperidine] and 9.25 g of sodium carbonate in 200 cc of chloroform. The reaction mixture is boiled at reflux for 17 hours, is filtered, concentrated by evaporation, the evaporation residue is placed on a column of 100 g of silica gel and elution is effected with chloroform containing 1% of methanol. The evaporation residue of the eluate is dissolved in acetone and made weakly acid to Congo red with hydrogen chloride in ether. The 5-[4-(9-xanthenylidene)piperidino]-2-pentanone hydrochloride which precipitates immediately is recrystallized from alcohol. M.P. 248°–251° (decomp.).

The following [4-(9-xanthenylidene)-piperidino]alkanone derivatives may also be obtained in a manner analogous to that described in Example 1, by reaction of a halogen alkanone with a correspondingly substituted 4-(9-xanthenylidene)piperidine derivative:
4-[4-(9-xanthenylidene)piperidino]-2-butanone,
4-[4-(9-xanthenylidene)piperidino]-3-methyl-2-butanone,
5-[4-(9-xanthenylidene)piperidino]-3-pentanone,
5-[4-(9-xanthenylidene)piperidino]-2-methyl-3-pentanone,
6-[4-(3-chloro-9-xanthenylidene)piperidino]-2-hexanone,
5[4-(2-trifluoromethyl-9-xanthenylidene)piperidino]-2,2-dimethyl-3-pentanone,
4-[4-(2-chloro-9-xanthenylidene)piperidino]-2-butanone,
4-[4-(2-fluoro-9-xanthenylidene)piperidino]-2-butanone,
4-[4-(3-methoxy-9-xanthenylidene)piperidino]-2-butanone,
4-[4-(2-methylthio-9-xanthenylidene)piperidino]-2-butanone,
4-[4-(2-methyl-9-xanthenylidene)piperidino]-2-butanone,
5[4-(2,7-dichloro-9-xanthenylidene)piperidino]-2-pentanone.

EXAMPLE 2

4-[4-(9-xanthenylidene)piperidino]-2-butanone

One drop of tribenzylmethyl ammonium hydroxide is added to a solution of 7 g of 4-(9-xanthenylidene)piperidine in 70 cc of ethanol, 4.38 cc of methylvinylketone are then added dropwise, and stirring is effected at 50° for 4 hours. The reaction mixture is then concentrated by evaporation in a vacuum, the residue is dissolved in chloroform, extraction is effected with water, and after drying over magnesium sulphate, concentration is effected by evaporation. The partially crystalline residue is triturated with ether/petroleum ether 1:1 and recrystallized from ethanol. M.P. of the title compound 111°–112°.

EXAMPLE 3

4-[4-(9-xanthenylidene)piperidino]-3-methyl-2-butanone

The crude title compound is obtained in a manner analogous to that described in Example 2, from 2 g of 4-(9-xanthenylidene)piperidine and 1.3 g of isopropenylmethylketone. After chromatography of the crude product on silica gel, the hydrochloride is produced with hydrogen chloride in ether. After crystallization from methanol/acetone the hydrochloride has an M.P. of 192°–193°.

The following [4-(9-xanthenylidene)-piperidino]alkanone derivatives may also be obtained in a manner analogous to that described in Example 2, by reaction of an alkylvinylketone with a correspondingly substituted 4-(9-xanthenylidene)piperidine derivative:
4-[4-(9-xanthenylidene)piperidino]-2-butanone,
5-[4-(9-xanthenylidene)piperidino]-3-pentanone,
5-[4-(9-xanthenylidene)piperidino]-2-methyl-3-pentanone,
4-[4-(3-chloro-9-xanthenylidene)piperidino]-2-butanone,
5-[4-(2-trifluoromethyl-9-xanthenylidene)piperidino]-2,2-dimethyl-3-pentanone,
4-[4-(2-chloro-9-xanthenylidene)piperidino]-2-butanone,
4-[4-(2-fluoro-9-xanthenylidene)piperidino]-2-butanone,
4-[4-(2-methoxy-9-xanthenylidene)piperidino]-2-butanone,
4-[4-(2-methylthio-9-xanthenylidene)piperidino]-2-butanone,
4-[4-(3-methyl-9-xanthenylidene)piperidino]-2-butanone.

EXAMPLE 4

5-[4-(9,10-dihydro-9,9-dimethyl-10-anthracenylidene)-piperidino]-2-pentanone 7.2 g of sodium carbonate are added to a solution of 8.5 g of 4-(9,10-dihydro-9,9-dimethyl-10-anthracenylidene)-piperidine in 200 cc of chloroform. 5.86 g of 5-bromo-2-pentanone in 40 cc of chloroform are then added dropwise, and the mixture is subsequently boiled at reflux for 17 hours. After cooling, the precipitate is filtered off, the filtrate is extracted twice with water, dried over magnesium sulphate and concentrated by evaporation. The residue is filtered over a column of 150 g of silica gel. The fraction eluted with chloroform containing 1% of methanol is dissolved in isopropanol and acidified with hydrogen chloride in ether, whereupon the hydrochloride of the title compound crystallizes. M.P. after recrystallization from methanol/ether 280°–284° (decomp.).

The starting material is produced as follows:
(a) A solution of 9.5 g of 4-(9,10-dihydro-9,9-dimethyl-10-anthracenylidene)-1-methylpiperidine in 100 cc of toluene is added dropwise at 90° within 1 hour to a solution of 8.2 cc of chloroformic acid ethyl ester in 30 cc of toluene, and the mixture is subsequently boiled at reflux for 17 hours. After cooling, extraction is effected thrice with water, drying over magnesium sulphate and concentration by evaporation are effected. The residue is then boiled for 1 hour with a solution of 13.3 g of potassium hydroxide in 90 cc of n-butanol. After cooling, dilution is effected with ½ liter of water and extraction is effected 4 times with benzene. The combined extracts are washed with saturated common salt solution, dried and concentrated by evaporation. The residue, a viscous, yellow-brown oil, is crude 4-(9,10-dihydro-9,9-dimethyl-10-anthracenylidene)-piperidine and is used for the next reaction as crude product.

The following [4-(9,10-dihydro-9,9-dialkyl-10-anthracenylidene)piperidino]alkanone derivatives may also be obtained in a manner analogous to that described in Example 4, by reaction of a halogen alkanone with a correspondingly substituted 4-(9,10-dihydro-9,9-dialkyl-10-anthracenylidene)piperidine derivative:
4-[4-(9,10-dihydro-9,9-dimethyl-10-anthracenylidene)-piperidino]-2-butanone,
5-[4-(2-chloro-9,10-dihydro-9,9-dimethyl-10-anthracenylidene)piperidino]-2-pentanone,
5-[4-(2,7-dichloro-9,10-dihydro-9,9-dimethyl-10-anthracenylidene)piperidino]-3-pentanone,
6-[4-(9,10-dihydro-2-methoxy-9,9-dimethyl-10-anthracenylidene)piperidino]-2-methyl-3-hexanone,
4-[4-(9,10-dihydro-9,9-dimethyl-1-methyloxy-10-anthracenylidene)piperidino]-3-methyl-2-butanone,
5-[4-(9,10-dihydro-2,9,9-trimethyl-10-anthracenylidene)-piperidino]-2-pentanone.

EXAMPLE 5

4-[4-(10,11-dihydro-5-dibenzo[a,d]-cycloheptenylidene)piperidino]-2-butanone 5.1 g of methylvinylketone are added dropwise at 70° to a solution of 10 g of 4-(10,11-dihydro-5-dibenzo[a,d]cycloheptenylidene)piperidine [M.P. 113°–114°, produced in a manner analogous to that described in Example 4 (a), from 4-(10,11-dihydro-5-dibenzo[a,d]cycloheptenylidene)-1-methylpiperidine] in 100 cc of ethanol, and the mixture is boiled at reflux for 1½ hours. The reaction mixture is then concentrated by evaporation in a vacuum, the residue is dissolved in acetone, the solution is made acid with hydrogen chloride in ether, is again concentrated by evaporation, and the residue is crystallized first from acetone/ether and then from isopropanol/ether. The hydrochloride of the title compound has an M.P. over 300°.

EXAMPLE 6

4-[4-(10,11-dihydro-5-dibenzo[a,d]cycloheptenylidene)-piperidino]-3-methyl-2-butanone The crude title compound is obtained in a manner analogous to that described in Example 5, from 2 g of 4-(10,11-dihydro-5-dibenzo[a,d]cycloheptenylidene)-piperidine and 1.25 g of isopropenylmethylketone. After chromatography of the crude product on silica gel, the hydrochloride is produced with hydrogen chloride in ether and recrystallized from methanol/acetone. M.P. over 275°.

The following [4-(10,11-dihydro-5-dibenzo-[a,d]cycloheptenylidene)piperidino]alkanone or [4-(5-dibenzo[a,d]cycloheptenylidene)piperidino]alkanone derivatives may also be obtained in a manner analogous to that described in Example 5, by reaction of a halogen alkanone with a correspondingly substituted 4-(10,11-dihydro-5-dibenzo[a,d]cycloheptenylidene)-piperidine or 4-(5-dibenzo[a,d]cycloheptenylidene)-piperidine derivative:
4-[4-(5-dibenzo[a,d]cycloheptenylidene)piperidino]-2-butanone,
4-[4-(3,7-dichloro-10,11-dihydro-5-dibenzo[a,d]-cycloheptenylidene)piperidino]-3-methyl-2-butanone,
5-[4-(2-methoxy-5-dibenzo[a,d]cycloheptenylidene)-piperidino]-3-pentanone,
5-[4-(10,11-dihydro-2-methyl-5-dibenzo[a,d]cycloheptenylidene)piperidino]-2-methyl-3-pentanone,
4-[4-(10,11-dihydro-3-methoxy-5-dibenzo[a,d]-cycloheptenylidene)piperidino]-2-butanone,
4-[4-(3-methyl-5-dibenzo[a,d]cycloheptenylidene)-piperidino]-2-butanone,
4-[4-(3-fluoro-10,11-dihydro-5-dibenzo[a,d]cycloheptenylidene)piperidino]-2-butanone,
4-[4-(10,11-dihydro-3-trifluoromethyl-5-dibenzo-[a,d]cycloheptenylidene)piperidino]-2-butanone,
4-[4-(3-trifluoromethyl-5-dibenzo[a,d]cycloheptenylidene)piperidino]-2-butanone,
4-[4-(3-fluoro-5-dibenzo[a,d]cycloheptenylidene)-piperidino]-2-butanone,
4-[4-(2-chloro-10,11-dihydro-5-dibenzo[a,d]cycloheptenylidene)piperidino]-2-butanone,
4-[4-(10,11-dihydro-3-methylthio-5-dibenzo[a,d]-cycloheptenylidene)piperidino]-2-butanone,
4-[4-(3-chloro-5-dibenzo[a,d]cycloheptenylidene)-piperidino]-2-butanone,
4-[4-(3-methylthio-5-dibenzo[a,d]cycloheptenylidene)-piperidino]-2-butanone.

EXAMPLE 7

5-[4-(10,11-dihydro-5-dibenzo[a,d]-cycloheptenylidene)piperidino]-2-pentanone 9.2 g of sodium carbonate are added to a solution of 10 g of 4-(10,11-dihydro-5-dibenzo[a,d]cycloheptenylidene)piperidine in 100 cc of chloroform, a solution of 7.2 g of 5-bromo-2-pentanone in 50 cc of chloroform is then added dropwise within 20 minutes, and the mixture is subsequently boiled at reflux for 17 hours. After cooling, the precipitate is filtered off, the filtrate is extracted twice with water, dried over magnesium sulphate and concentrated by evaporation. The residue is filtered over a column of 170 g of silica gel. The fraction eluted with chloroform containing 1% of methanol is dissolved in acetone and acidifed with hydrogen chloride in ether. After the addition of more ether, the hydrochloride of the title compound crystallizes. M.P. 235°–238°.

EXAMPLE 8

5-[4-(5-dibenzo[a,d]cycloheptenylidene)-piperidino]-2-pentanone 4-(5-dibenzo[a,d]cycloheptenylidene)piperidine is reacted in a manner analogous to that described in Example 7 with 5-bromo-2-pentanone. M.P. of the hydrochloride of the title compound 206°–207° after crystallization from isopropanol.

EXAMPLE 9

4-[4-(6,11-dihydrodibenzo[b,e]oxepin-11-ylidene)-piperidino]-2-butanone

A solution of 5.3 g of methylvinylketone in 10 cc of ethanol is added dropwise within 5 minutes to a solution of 13.8 g of 4-(6,11-dihydrodibenzo[b,e]oxepin-11-ylidene)piperidine in 50 cc of ethanol. The reaction mixture is boiled at reflux for 2 hours, is then completely concentrated at reduced pressure, and the oily residue is chromatographed on 250 g of silica gel with a mixture of chloroform/ethanol 95:5. The so purified title compound is subsequently converted into the hydrogen fumarate form. M.P. 173°–175°.

The starting material may be produced as follows:
(a) A solution of 96 g of chloroformic acid ethyl ester in 100 cc of benzene is added dropwise to a solution of 64 g of 4-(6,11-dihydrodibenzo[b,e]oxepin-11-ylidene)-1-methylpiperidine in 600 cc of benzene, and the mixture is heated in an oil bath of 100° for 4 hours. After cooling, the reaction mixture is filtered through diatomaceous earth, the filtrate is extracted with 2 N hydrochloric acid and water, dried over magnesium sulphate and completely concentrated at reduced pressure. The resulting urethane is split in a manner analogous to that described in Example 4 a), whereby crude 4-(6,11-dihydrodibenzo[b,e]oxepin-11-ylidene)piperidine is obtained as yellow-brown oil.

EXAMPLE 10

5-[4-(6,11-dihydrodibenzo[b,e]oxepin-11-ylidene)-piperidino]-2-pentanone

A solution of 10 g of 5-bromo-2-pentanone in 40 cc of chloroform is added dropwise within 10 minutes to a mixture of 13.8 g of 4-(6,11-dihydrodibenzo[b,e]oxepin-11-ylidene)piperidine and 12.7 g of sodium carbonate in 200 cc of chloroform, and the mixture is heated at reflux for 18 hours. After cooling, filtration is effected, the filtrate is washed with water, dried over magnesium sulphate, and the solvent is completely removed by distillation. The oily residue is then chromatographed on 250 g of silica gel with a mixture of chloroform/ethanol 95:5, and the so purified title compound is converted into the hydrogen fumarate form. M.P. 228°–230°.

The following [4-(6,11-dihydrodibenzo[b,e]-oxepin-11-ylidene)piperidino]alkanone derivatives may also be obtained in a manner analogous to that described in Example 10, by reaction of a halogen alkanone with a correspondingly substituted 4-(6,11-dihydrodibenzo[b,e]-oxepin-11-ylidene)piperidine derivative:

4-[4-(6,11-dihydro-2-trifluoromethyldibenzo[b,e]oxepin-11-ylidene)piperidino]-3-methyl-2-butanone,
6-[4-(2-fluoro-6,11-dihydrodibenzo[b,e]oxepin-11-ylidene)-piperidino]-3-hexanone,
5-[4-(2,9-dichloro-6,11-dihydrodibenzo[b,e]oxepin-11-ylidene)piperidino]-2-methyl-3-pentanone,
5-[4-(6,11-dihydro-2,7-dimethoxydibenzo[b,e]oxepin-11-ylidene)piperidino]-2,2-dimethyl-3-pentanone,
5-[4-(6,11-dihydro-2-methoxydibenzo[b,e]oxepin-11-ylidene)piperidino]-2-pentanone,
5-[4-(2-chloro-6,11-dihydrodibenzo[b,e]oxepin-11-ylidene)piperidino]-2-pentanone,
4-[4-(6,11-dihydro-4-methyldibenzo[b,e]oxepin-11-ylidene)piperidino]-2-butanone,
5-[4-(6,11-dihydro-2-methyldibenzo[b,e]oxepin-11-ylidene)piperidino]-2-pentanone,
4-[4-(6,11-dihydro-2-methylthiodibenzo[b,e]oxepin-11-ylidene)piperidino]-2-butanone.

EXAMPLE 11

4-[4-(6,11-dihydrodibenzo[b,e]thiepin-11-ylidene)-piperidino]-2-butanone

A solution of 2.8 g of methylvinylketone in 5 cc of ethanol is added dropwise within 2 minutes to a solution of 7.8 g of 4-(6,11-dihydrodibenzo[b,e]thiepin-11-ylidene)piperidine [M.P. of the fumarate 245°–247°, produced in a manner analogous to that described in Example 9(a), from 4-(6,11-dihydrodibenzo[b,e]thiepin-11-ylidene)-1-methylpiperidine] in 25 cc of ethanol. The reaction mixture is heated at reflux for 1 hour, is then completely concentrated at reduced pressure, and the oily residue, the title compound, is converted into the hydrogen fumarate form. M.P. 180°–182° (decomp.) from ethanol.

EXAMPLE 12

5-[4-(6,11-dihydrodibenzo[b,e]thiepin-11-ylidene)-piperidino]-2-pentanone

A solution of 10 g of 5-bromo-2-pentanone in 40 cc of chloroform is added dropwise within 10 minutes to a mixture of 14.7 g of 4-(6,11-dihydrodibenzo[b,e]thiepin-11-ylidene)piperidine and 12.7 g of potassium carbonate in 200 cc of chloroform, and the mixture is heated at reflux for 18 hours. After cooling, filtration is effected, the filtrate is washed with water, dried over magnesium sulphate, and the solvent is completely removed by distillation. The oily residue is then chromatographed on 200 g of silica gel with a mixture of chloroform/ethanol 9:1, and the so purified title compound is converted into the hydrogen fumarate form. M.P. 215°–218° from ethanol.

The following [4-(6,11-dihydrodibenzo[b,e]-thiepin-11-ylidene)piperidino]alkanone derivatives may also be obtained in a manner analogous to that described in Example 12, by reaction of a halogen alkanone with a correspondingly substituted 4-(6,11-dihydrodibenzo[b,e]-thiepin-11-ylidene)piperidine derivative:

4-[4-(6,11-dihydro-2-trifluoromethyldibenzo[b,e]thiepin-11-ylidene)piperidino]-3-methyl-2-butanone,
6-[4-(2-fluoro-6,11-dihydrodibenzo[b,e]thiepin-11-ylidene)piperidino]-3-hexanone,
5-[4-(2,9-dichloro-6,11-dihydrodibenzo[b,e]thiepin-11-ylidene)piperidino]-2-methyl-3-pentanone, 5-[4-(6,11-dihydro-2,7-dimethoxydibenzo[b,e]thiepin-11-ylidene)piperidino]-2,2-dimethyl-3-pentanone,
5-[4-(6,11-dihydro-2-methoxydibenzo[b,e]thiepin-11-ylidene)piperidino]-2-pentanone,
5-[4-(2-chloro-6,11-dihydrodibenzo[b,e]thiepin-11-ylidene)piperidino]-2-pentanone,
4-[4-(3-chloro-6,11-dihydrodibenzo[b,e]thiepin-11-ylidene)piperidino]-2-butanone,
5-[4-(6,11-dihydro-2-methyldibenzo[b,e]thiepin-11-ylidene)piperidino]-2-pentanone,
4-[4-(6,11-dihydro-2-methylthiodibenzo[b,e]thiepin-11-ylidene)piperidino]-2-butanone.

EXAMPLE 13

4-[4-(9,10-dihydro-4H-benzo[4,5]cyclohepta-[1,2-b]thiophen-4-ylidene)piperidino]-2-butanone A solution of 5.8 g of methylvinylketone in 15 cc of dioxane is added dropwise within 10 minutes to a solution of 15.0 g of 9,10-dihydro-4-(4-piperidylidene)-4H-benzo[4,5]cyclohepta[1,2-b]thiophene in 60 cc of dioxane and 0.3 cc of benzyltrimethyl ammonium hydroxide. The reaction mixture is stirred at room temperature for 1 hour, is allowed to stand over night, is decolourized with active charcoal and evaporated to dryness. The oily residue, the title compound, is converted into the hydrobromide form. M.P. 234°-235° from ethanol.

The following [4-(9,10-dihydro-4H-benzo[4,5]-cyclohepta[1,2-b]thiophen-4-ylidene)piperidino]alkanone or [4-(4H-benzo[4,5]cyclohepta[1,2-b]thiophen-4-ylidene)-piperidino]alkanone derivatives may also be obtained in a manner analogous to that described in Example 13, by reaction of an alkylvinylketone with a correspondingly substituted 9,10-dihydro-4-(4-piperidylidene)-4H-benzo[4,5]-cyclohepta[1,2-b]thiophene or 4-(4-piperidylidene)-4H-benzo[4,5]cycl ohepta[1,2-b]thiophene derivative:

4-[4-(6-fluoro-9,10-dihydro-4H-benzo[4,5]cyclohepta[1,2-b]-thiophen-4-ylidene)piperidino]-3-methyl-2-butanone,
5-[4-(9,10-dihydro-7-methylthio-4H-benzo[4,5]cyclohepta-[1,2-b]thiophen-4-ylidene)piperidino]-3-pentanone,
5-[4-(7-fluoro-4H-benzo[4,5]cyclohepta[1,2-b]thiophen-4-ylidene)piperidino]-2-methyl-3-pentanone,
5-[4-(9,10-dihydro-6-methyl-4H-benzo[4,5]cyclohepta[1,2-b]-thiophen-4-ylidene)piperidino]-2,2-dimethyl-3-pentanone,
4-[4-(2-chloro-4H-benzo[4,5]cyclohepta[1,2-b]thiophen-4-ylidene)piperidino]-2-butanone,
4-[4-(9,10-dihydro-2-methyl-4H-benzo[4,5]cyclohepta-[1,2-b]thiophen-4-ylidene)piperidino]-2-butanone,
4-[4-(6-methoxy-4H-benzo[4,5]cyclohepta[1,2-b]thiophen-4-ylidene)piperidino]-2-butanone,
4-[4-(2,6-dimethyl-4H-benzo[4,5]cyclohepta[1,2-b]-thiophen-4-ylidene)piperidino]-2-butanone.

EXAMPLE 14

4-[4-(4H-benzo[4,5]cyclohepta[1,2-b]-thiophen-4-ylidene)piperidino]-2-butanone

The title compound is produced in a manner analogous to that described in Example 13, from 7.5 g of 4-(4-piperidylidene)-4H-benzo[4,5]cyclohepta[1,2-b]-thiophene and 0.15 g of benzyltrimethyl ammonium hydroxide n 30 cc of dioxane and 2.9 g of methylvinylketone in 10 cc of dioxane. M.P. of the hydrobromide form 133°-136° from ethanol/ether.

EXAMPLE 15

5-[4-(9,10-dihydro-4H-benzo[4,5]cyclohepta-[1,2-b]thiophen-4-ylidene)piperidino]-2-pentanone A solution of 10.0 g of 5-bromo-2-pentanone in 100 cc of chloroform is added dropwise within 10 minutes to a mixture of 18.0 g of 9,10-dihydro-4-(4-piperidylidene)-4H-benzo[4,5]cyclohepta[1,2-b]thiophene hydrobromide and 12.0 g of sodium carbonate in 200 cc of chloroform, and the mixture is heated at reflux for 7 hours. After the addition of a further 5 g of sodium carbonate, the mixture is stirred at the boil for 16 hours, is diluted with 100 cc of dimethyl formamide, filtered whilst hot, and the filtrate is washed with water. The organic solution is dried over sodium sulphate, the solvent is removed by evaporation, and the oily residue, the title compound, is converted into the hydrobromide form. M.P. 218°-220° from ethanol.

The following [4-(9,10-dihydro-4H-benzo[4,5]-cyclohepta[1,2-b]thiophen-4-ylidene)piperidino]alkanone or [4-(4H-benzo[4,5]cyclohepta[1,2-b]thiophen-4-ylidene)-piperidino]alkanone derivatives may also be obtained in a manner analogous to that described in Example 15, by reaction of a halogen alkanone with a correspondingly substituted 9,10-dihydro-4-(4-piperidylidene)-4H-benzo[4,5]-cyclohepta[1,2-b]thiophene or 4-(4-piperidylidene)-4H-benzo[4,5]cyclohepta[1,2-b]thiophene derivative:

4-[4-(6-fluoro-9,10-dihydro-4H-benzo[4,5]cyclohepta-[1,2-b]thiophen-4-ylidene)piperidino]-3-methyl-2-butanone,
5-[4-(9,10-dihydro-7-methylthio-4H-benzo[4,5]cyclohepta-[1,2-b]thiophen-4-ylidene)piperidino]-3-pentanone,
5-[4-(7-fluoro-4H-benzo[4,5]cyclohepta[1,2-b]thiophen-4-ylidene)piperidino]-2-methyl-3-pentanone,
5-[4-(9,10-dihydro-6-methyl-4H-benzo[4,5]cyclohepta[1,2-b]-thiophen-4-ylidene)piperidino]-2,2-dimethyl-3-pentanone,
4-[4-(2-chloro-4H-benzo[4,5]cyclohepta[1,2-b]thiophen-4-ylidene)piperidino]-2-butanone,
4-[4-(9,10-dihydro-2-methyl-4H-benzo[4,5]cyclohepta-[1,2-b]thiophen-4-ylidene)piperidino]-2-butanone,
4-[4-(6-methoxy-4H-benzo[4,5]cyclohepta[1,2-b]thiophen-4-ylidene)piperidino]-2-butanone,
4-[4-(2,6-dimethyl-4H-benzo[4,5]cyclohepta[1,2-b]thiophen-4-ylidene)piperidino]-2-butanone,
6-[4-(2-chloro-6-methoxy-4H-benzo[4,5]cyclohepta[1,2-b]-thiophen-4-ylidene)piperidino]-2-hexanone,
5-[4-(2-methyl-4H-benzo[4,5]cyclohepta[1,2-b]thiophen-4-ylidene)piperidino]-2-pentanone,
5-[4-(2-chloro-9,10-dihydro-4H-benzo[4,5]cyclohepta[1,2-b]-thiophen-4-ylidene)piperidino]-2-pentanone.

EXAMPLE 16

5-[4-(4H-benzo[4,5]cyclohepta[1,2-b]-thiophen-4-ylidene)piperidino]-2-pentanone

The title compound is produced in a manner analogous to that described in Example 15, from 7.5 g of 4-(4-piperidylidene)-4H-benzo[4,5]cyclohepta[1,2-b]-thiophene, 7.1 g of sodium carbonate and 5.3 g of 5-bromo-2-pentanone in 300 cc of chloroform. M.P. of the hydrobromide form 248°-251° from methanol/ethanol.

EXAMPLE 17

4-[4-(thieno[2,3-b][1]benzothiopyran-4-ylidene)-piperidino]-2-butanone 0.3 cc of benzyltrimethyl ammonium hydroxide are first added to a solution of 11.8 g of 4-(4-piperidylidene)thieno[2,3-b][1]benzothiopyrane in 70 cc of dioxane, and a solution of 5.1 g of methylvinylketone in 20 cc of dioxane is added dropwise within 15 minutes. The reaction mixture is then stirred at room temperature for 30 minutes, and at 55° for 6½ hours, is cooled, filtered through Hyflo and evaporated to dryness. The oily residue is chromatographed on 300 g of silica gel with a 1% methanol solution in methylene chloride, and the title compound is crystallized as hydrogen fumarate from methanol/ether. M.P. 144°–146° (sintering from 136°).

The starting material may be produced as follows:

(a) A solution of 21.5 g of 4-(1-methyl-4-piperidylidene)thieno[2,3-b][1]benzothiopyrane in 150 cc of absolute benzene is added dropwise at 50°–60° to a solution of 25.4 g of chloroformic acid ethyl ester in 150 cc of absolute benzene. The reaction mixture is then heated to the boil for 3½ hours, is cooled to room temperature, washed with 1 N hydrochloric acid and with water, dried over magnesium sulphate and evaporated to dryness. The crude 4-(1-carbethoxy-4-piperidylidene)-thieno[2,3-b][1]benzothiopyrane is used for the next reaction without purification.

(b) A mixture of 19.0 g of the product obtained above, 7.6 g of potassium hydroxide and 120 cc of n-butanol is heated to the boil with stirring for 5½ hours. After removing the solvent by evaporation, dilution is effected with water and benzene, the organic phase is separated, washed with water until neutral and extracted with 2 N tartaric acid. The acid extracts are washed with ether, made alkaline with concentrated caustic soda solution, and the basic product is extracted with methylene chloride. After washing with water, drying over sodium sulphate and removing the solvent by evaporation, 4-(4-piperidylidene)thieno[2,3-b][1]benzothiopyrane is obtained as viscous oil. M.P. of the hydrogen fumarate form 220°–222° from methanol.

The following [4-(thieno[2,3-b][1]benzothiopyran-4-ylidene)piperidino]alkanone derivatives may also be obtained in a manner analogous to that described in Example 17, by reaction of an alkylvinylketone with a correspondingly substituted 4-(4-piperidylidene)thieno-[2,3-b][1]benzothiopyrane derivative:

4-[4-(thieno[2,3-b][1]benzothiopyran-4-ylidene)-piperidino]-3-methyl-2-butanone,
5-[4-(7-trifluoromethylthieno[2,3-b][1]benzothiopyran-4-ylidene)piperidino]-3-pentanone,
5-[4-(7-chlorothieno[2,3-b][1]benzothiopyran-4-ylidene)-piperidino]-2,2-dimethyl-3-pentanone.

EXAMPLE 18

5-[4-(thieno[2,3-b][1]benzothiopyran-4-ylidene)-piperidino]-2-pentanone

A solution of 6.3 g of 5-bromo-2-pentanone in 60 cc of chloroform is added dropwise within 10 minutes to a mixture of 9.0 g of 4-(4-piperidylidene)thieno[2,3-b][1]-benzothiopyrane and 8.4 g of calcinated sodium carbonate in 90 cc of chloroform, and the mixture is heated to the boil while stirring for 16 hours. After cooling to room temperature, the inorganic part is removed by filtration, the filtrate is evaporated to dryness and the residue is chromatographed over neutral aluminium oxide with a 1% methanol solution in methylene chloride. The title compound is converted into the hydrogen fumarate form in methanol. M.P. 149°–151° from methanol/ether.

The following [4-(thieno[2,3-b][1]benzothiopyran-4-ylidene)piperidino]alkanone derivatives may also be obtained in a manner analogous to that described in Example 18, by reaction of a halogen alkanone with a correspondingly substituted 4-(4-piperidylidene)thieno-[2,3-b][1]benzothiopyrane derivative:

4-[4-(thieno[2,3-b][1]benzothiopyran-4-ylidene)-piperidino]-3-methyl-2-butanone,
5-[4-(7-trifluoromethylthieno[2,3-b][1]benzothiopryan-4-ylidene)piperidino]-3-pentanone,
5-[4-(7-chlorothieno[2,3-b][1]benzothiopyran-4-ylidene)-piperidino]-2,2-dimethyl-3-pentanone,
6-[4-(7-chlorothieno[2,3-b][1]benzothiopyran-4-ylidene)-piperidino]-2-hexanone,
5-[4-(6-fluorothieno[2,3-b][1]benzothiopyran-4-ylidene)-piperidino]-2-pentanone,
5-[4-(7-methoxythieno[2,3-b][1]benzothiopyran-4-ylidene)-piperidino]-2-pentanone,
5-[4-(7-methylthiothieno[2,3-b][1]benzothiopyran-4-ylidene)piperidino]-2-pentanone,
5-[4-(thieno[2,3-b][1]benzothiopyran-4-ylidene)-piperidino]-2-methyl-3-pentanone.

EXAMPLE 19

5-[4-(7-chlorothieno[2,3-b][1]benzothiopyran-4-ylidene)piperidino]-2-pentanone

The title compound is produced in a manner analogous to that described in Example 18, from 8.5 g of 7-chloro-4-(4-piperidylidene)thieno[2,3-b][1]benzothiopyrane, 7.1 g of calcinated sodium carbonate and 5.3 g of 5-bromo-2-pentanone in 140 cc of chloroform, and is then chromatographed. It is then converted into the hydrobromide form. M.P. 180°–181° from acetone.

The starting material may be produced in a manner analogous to that described in Example 17 (a), (b):

(a) 4-(1-carbethoxy-4-piperidylidene)-7-chlorothieno[2,3-b][1]benzothiopyrane from 54.0 g of 7-chloro-4-(1-methyl-4-piperidylidene)thieno[2,3-b][1]benzothiopyrane and 55.0 g of chloroformic acid ethyl ester in 800 cc of benzene. The oily crude product is used for the next reaction without further purification.

(b) 7-chloro-4-(4-piperidylidene)thieno[2,3-b][1]-benzothiopyrane from 33.5 g of the product obtained above, 12.1 g of potassium hydroxide and 200 cc of n-butanol. M.P. of the hydrochloride form: over 300° (decomp.) from methanol/ether.

EXAMPLE 20

The following compounds may be obtained in manner analogous to that described in Example 13 using appropriate starting materials in approximately equivalent amounts. Characterisation was effected by thin layer chromatography using Kieselgel as absorbant and a mixture of benzene/ethanol/ammonia (ratio 84:15:1) as the mobile phase.

(a) 5-[4-(9,10-Dihydro-6-methyl-4H-benzo[4,5]-cyclohepta[1,2-b]thiophen-4-ylidene)piperidino]-2,2-dimethyl-3-pentanone, Rf value: 5.0;

(b) 4-[4-(2-chloro-4H-benzo[4,5]cyclohepta-[1,2-b]thiophen-4-ylidene)piperidino]-2-butanone, in the form of the hydrogen fumarate, Rf value 5.5 and (c) 4-[4-(9,10-dihydro-2-methyl-4H-benzo[4,5]-cyclohepta[1,2-b]thiophen-4-ylidene)piperidino]-2-butanone, Rf value 6.2.

The compounds of formula I have not been described in the literature.

The compounds of formula I are useful because they possess pharmacological activity in animals. In particular, the compounds of formula I are useful as sedative-neuroleptic agents for example for the treatment of excitation conditions and as muscle-relaxing agents for example for the treatment of muscle spasms, as indicated by an inhibition of spontaneous motor activity in the jiggle test in mice on p.o. administration of from 5 to 100 mg/kg animal body weight of the compounds and an inhibition of the climbing capacity in mice in the climbing test on i.p. administration of from 0.3 to 20 mg/kg animal body weight of the compounds.

The compounds of formula I are furthermore useful as sleep-promoting agents, as indicated in the Pentothal test by a prolongation of the loss of the righting reflex induced by Pentothal in mice on i.p. administration of from 3 to 100 mg/kg animal body weight of the compounds and in the Barbital test by a loss of the righting reflex in rats pretreated with an amount of Barbital insufficient to suppress completely the righting reflex on i.p. administration of from 4 to 80 mg/kg animal body weight of the compounds.

For the above-mentioned use the dosage will, of course, vary depending on the compound employed, mode of administration and therapy desired. However, in general, satisfactory results are obtained when administered at a daily dosage of from about 0.1 to about 100, or to about 200 for muscle-relaxing use, mg/kg animal body weight, conveniently given in divided doses 2 to 4 times a day or in sustained release form. For the larger mammals, the total daily dosage is in the range from about 5 to about 200 mg, and dosage forms suitable for oral administration comprise from about 1 mg to about 100 mg of the compounds admixed with a solid or liquid pharmaceutical carrier or diluent.

The compounds of formula I may be administered in pharmaceutically acceptable acid addition salt form. Such acid addition salt forms exhibit the same order of activity as the free base forms and are readily prepared in conventional manner. Representative acid addition salt forms include organic acid salt forms such as the hydrogen maleate, fumarate, tartrate and methane sulphonate and mineral acid salt forms such as the hydrochloride, hydrobromide and sulphate. A pharmaceutical composition may comprise a compound of formula I, in free base form or in pharmaceutically acceptable acid addition salt form, in association with a pharmaceutical carrier or diluent. Such compositions conveniently contain more than 1% by weight of the compound of formula I and may be prepared by conventional techniques to be in conventional forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastrointestinal tract and thereby provide sustained action over a long period.

The preferred compositions from the standpoint of ease of administration are solid compositions, particularly solid-filled gelatin capsules and tablets.

What is claimed is:

1. A compound of the formula,

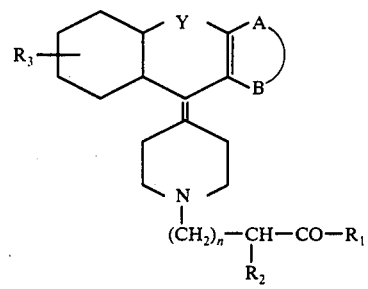

wherein
*n* is 1, 2 or 3,
R₁ is lower alkyl,
R₂ is hydrogen or lower alkyl,
R₃ is hydrogen, chlorine, bromine, fluorine, trifluoromethyl, lower alkyl, lower alkoxy or lower alkylthio,
A and B together with the double bond form a benzene ring, or a benzene ring substituted by chlorine, bromine, fluorine, trifluoromethyl, lower alkyl, lower alkoxy or lower alkylthio, or
A is sulphur and
A and B together with the double bond form a thiophene ring, or a thiophene ring substituted in the α position to the sulphur by chlorine, bromine or lower alkyl, and
Y is ethylene or vinylene, when A and B together with the double bond form a benzene ring, or a benzene ring substituted by chlorine, bromine, fluorine, trifluoromethyl, lower alkyl, lower alkoxy or lower alkylthio, or when A is sulphur and A and B together with the double bond form a thiophene ring, or a thiophene ring substituted in the α position to the sulphur by chlorine, bromine or lower alkyl, or
Y is oxygen, methyleneoxy, methylenethio or a group

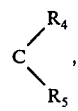

wherein R₄ and R₅ are independently lower alkyl, when A and B together with the double bond form a benzene ring, or a benzene ring substituted by chlorine, bromine, fluorine, trifluoromethyl, lower alkyl, lower alkoxy or lower alkylthio, or
Y is sulphur, when A is sulphur and A and B together with the double bond form a thiophene ring, or a pharmaceutically acceptable acid addition salt thereof.

2. A pharmaceutical composition comprising a soparifically effective amount of a compound of claim 1 in association with a pharmaceutical carrier or diluent.

3. A method of promoting sleep in animals which comprises administering to an animal in need of such treatment a therapeutically effective amount of a compound of claim 1.

4. A compound of claim 1, wherein Y is ethylene or vinylene, A is sulphur and A and B together with the double bond from a thiophene ring or a thiophene ring substituted in the α-position to the sulphur by chlorine, bromine or lower alkyl.

5. A compound of claim 1, wherein Y is sulphur, A is sulphur and A and B together with the double bond form a thiophene ring.

6. The compound of claim 1 which is 5-[4-(9-xanthenylidene)piperidino]-2-pentanone.

7. The compound of claim 1 which is 4-[4-(9-xanthenylidene)piperidino]-2-butanone.

8. The compound of claim 1 which is 4-[4-(9-xanthenylidene)piperidino]-3-methyl-2-butanone.

9. The compound of claim 1 which is 5-[4-(9,10-dihydro-9,9-dimethyl-10-anthracenylidene)-piperidino]-2-pentanone.

10. The compound of claim 1 which is 4-[4-(10,11-dihydro-5-dibenzo[a,d]cycloheptenylidene)-piperidino]-2-butanone.

11. The compound of claim 1 which is 4-[4-(10,11-dihydro-5-dibenzo[a,d]cycloheptenylidene)-piperidino]-3-methyl-2-butanone.

12. The compound of claim 1 which is 5-[4-(10,11-dihydro-5-dibenzo[a,d]cycloheptenylidene)-piperidino]-2-pentanone.

13. The compound of claim 1 which is 5-[4-(5-dibenzo[a,d]cycloheptenylidene)piperidino]-2-pentanone.

14. The compound of claim 1 which is 4-[4-(6,11-dihydrodibenzo[b,e]oxepin-11-ylidene)piperidino]-2-butanone.

15. The compound of claim 1 which is 5-[4-(6,11-dihydrodibenzo[b,e]oxepin-11-ylidene)piperidino]-2-pentanone.

16. The compound of claim 1 which is 4-[4-(6,11-dihydrodibenzo[b,e]thiepin-11-ylidene)piperidino]-2-butanone.

17. The compound of claim 1 which is 5-[4-(6,11-dihydrodibenzo[b,e]thiepin-11-ylidene)piperidino]-2-pentanone.

18. The compound of claim 1 which is 4-[4-(9,10-dihydro-4H-benzo[4,5]cyclohepta[1,2-b]thiophen-4-ylidene)piperidino]-2-butanone.

19. The compound of claim 1 which is 4[4-(4H-benzo[4,5]cyclohepta[1,2-b]thiophen-4-ylidene)-piperidino]-2-butanone.

20. The compound of claim 1 which is 5-[4-(9,10-dihydro-4H-benzo[4,5]cyclohepta[1,2-b]thiophen-4-ylidene)piperidino]-2-pentanone.

21. The compound of claim 1 which is 5-[4-(4H-benzo[4,5]cyclohepta[1,2-b]thiophen-4-ylidene)piperidino]-2-pentanone.

22. The compound of claim 1 which is 4-[4-(thieno[2,3-b][1]benzothiopyran-4-ylidene)piperidino]-2-butanone.

23. The compound of claim 1 which is 5-[4-(thieno[2,3-b][1]benzothiopyran-4-ylidene)piperidino]-2-pentanone.

24. The compound of claim 1 which is 5-[4-(7-chlorothieno[2,3-b][1]benzothiopyran-4-ylidene)piperidino]-2-pentanone.

25. A compound of claim 1 wherein Y is ethylene or vinylene and A and B together with the double bond form an unsubstituted thiophene ring.

26. A pharmaceutical composition according to claim 2 in which the compound is 5-[4-(9,10-dihydro-4H-benzo[4,5]cyclohepta[1,2-b]thiophen-4-ylidene)piperidino]-2-pentanone.

27. A method according to claim 3 in which 5 to 200 milligrams of the compound are administered daily.

28. A method according to claim 3 in which 1 to 100 milligrams of the compound are administered per unit dose.

29. A method according to claim 3 in which the compound is 5-[4-(9,10-dihydro-4H-benzo[4,5]cyclohepta[1,2-b]thiophen-4-ylidene)piperidino]-2-pentanone.

* * * * *